United States Patent [19]

Higgins et al.

[11] Patent Number: 4,545,382
[45] Date of Patent: Oct. 8, 1985

[54] SENSOR FOR COMPONENTS OF A LIQUID MIXTURE

[75] Inventors: Irving J. Higgins, Wilden; Hugh A. O. Hill, Oxford; Elliot V. Plotkin, Bedford, all of England

[73] Assignee: Genetics International, Inc., Cambridge, Mass.

[21] Appl. No.: 436,106

[22] Filed: Oct. 22, 1982

[30] Foreign Application Priority Data

Oct. 23, 1981 [GB] United Kingdom ............... 8132034

[51] Int. Cl.$^4$ ............................................. A61B 5/00
[52] U.S. Cl. ................................... 128/635; 204/403; 204/415
[58] Field of Search ................. 128/635; 204/403, 415

[56] References Cited

U.S. PATENT DOCUMENTS

| | | | |
|---|---|---|---|
| 3,506,544 | 4/1970 | Silverman et al. | 204/1 |
| 3,591,480 | 7/1971 | Neff et al. | 204/195 |
| 3,623,960 | 4/1970 | Williams | 204/195 |
| 3,770,607 | 11/1973 | Williams | 204/195 |
| 3,838,033 | 8/1972 | Mindt et al. | 204/403 |
| 4,005,002 | 1/1977 | Racine et al. | 204/195 |
| 4,129,478 | 12/1978 | Racine et al. | 204/1 |
| 4,144,143 | 3/1979 | Hawkridge et al. | 204/72 |
| 4,224,125 | 9/1980 | Nakamura et al. | 204/195 |
| 4,356,074 | 10/1982 | Johnson | 204/195 |
| 4,388,166 | 5/1982 | Suzuki et al. | 204/403 |
| 4,442,841 | 4/1984 | Uehara et al. | 128/635 |

FOREIGN PATENT DOCUMENTS

| | | |
|---|---|---|
| 55-10581 | 1/1980 | Japan. |
| 55-10584 | 1/1980 | Japan. |
| 55-10583 | 1/1980 | Japan. |
| 0124060 | 9/1980 | Japan ................. 204/403 |

OTHER PUBLICATIONS

Hinkle (1973) Federation Proceedings 32(9):1988–1992.
Fujihira et al., (1974) Biochemical and Biophysical Research Communications 61(2):538–543.
Epton et al., (1978) J. Organometallic Chemistry 149:231–244.
Szentrimay et al. in D. Sawyer (Ed.) Electrochemical Studies of Biological Systems, Ch. 6, p. 143, (Am. Chem. Soc., Wash. D.C. 1977).
Yeh et al., (1976) J. Electrochemical Society 123:1334–1339.
Shinbo et al., Potentiometric Enzyme Electrode for Lactate, Am. Chem. Soc. 51 (No. 1):100–101 (1978).
Wingard et al., "Direct Coupling of Glucose Oxidase to Platinum and Possible Use For In Vivo Glucose Determination", Journal of Solid-Phase Biochemistry, 4, (No. 4):253 (1979).
Plotkin et al., "Methanol Dehydrogenase Bioelectrochemical Cell and Alcohol Detector", Biotechnology Letters, 3 (No. 4):187 (1981).

Primary Examiner—Lee S. Cohen

[57] ABSTRACT

A sensor electrode to detect one or more components in a liquid mixture comprises an electrically conductive material having at least an an external surface, the combination of an enzyme catalytic for a reaction of the desired component, and a mediator compound which transfers electrons from the enzyme to the electrode when such catalytic activity takes place. It can be used as an in vivo glucose sensor either with a silver electrode coated with e.g. glucose oxidase and a polyviologen as the mediators, or with a particulate carbon electrode, glucose oxidase and chloranil or fluoranil as mediator. Another system is to use bacterial glucose dehydrogenase or glucose oxidase as the enzyme and/or ferrocene or a ferrocene derivative as the mediators compound to give electrodes with improved linearity, speed of response and insensitivity to oxygen.

19 Claims, 7 Drawing Figures

SENSOR FOR COMPONENTS OF A LIQUID MIXTURE

BACKGROUND OF THE INVENTION

This invention relates to equipment and methods for detecting the presence of, measuring the amount of, and/or monitoring the level of one or more selected components in a liquid mixture.

While use may be made of this invention in chemical industry, especially where complex mixtures are encountered (e.g. in food chemistry or biochemical engineering) it is of particular value in biological investigation and control techniques. More particularly, it lends itself to animal or human medicine, and in particular to in vivo measuring or monitoring of components in body fluids.

For convenience, the invention will be described with reference primarily to one such procedure, the determination of glucose in a diabetic human subject, by the use of equipment which, while usable on a specific or occasional basis also lends itself to temporary or permanent implantation. However, while the provision of an implantable glucose sensor is a major object of the invention other and broader objects are not hereby excluded.

In vivo glucose sensors have already been proposed. One proposal is based on direct oxidation of glucose at a catalytic platinum electrode (see Hormone and Metabolic Research, Supplement Series No. 8, pp 10–12 (1979)) but suffers from the drawback of being nonspecific and of being easily poisoned by interfering substances. Another proposal, for a procedure more specific to glucose, involves the use of glucose oxidase on an oxygen electrode (Adv. Exp. Med. Biol, 50 pp 189–197 (1974)) but is not very responsive to the high glucose concentrations. Other systems using glucose oxidase have been proposed but not fully investigated for in vivo methods, see e.g. J. Solid-Phase Biochem. 4 pp 253–262 (1979).

The inventors have recently carried out in vitro studies of enzyme-catalysed reactions using a mediator in solution to transfer the electrons arising from the enzyme, during its action, directly to the electrode, as described in Biotechnology Letters 3 pp 187–192 (1981).

SUMMARY OF THE INVENTION

It has now been realised that mediator compounds can be associated with the sensor electrode structure thus rendering such electrodes available for use by in vivo methods.

In one aspect the present invention consists in a sensor electrode for use in liquid mixtures of components for detecting the presence of, measuring the amount of, and/or monitoring the level of, one or more selected components capable of undergoing an enzyme-catalysed reaction, the electrode being composed of electrically conductive material and comprising, at least at an external surface thereof, the combination of an enzyme and a mediator compound which transfers electrons to the electrode when the enzyme is catalytically active.

Preferably the electrode is designed to determine glucose in vivo. The enzyme is therefore preferably a glucose oxidase, or possibly a glucose dehydrogenase, for example a bacterial glucose dehydrogenase.

Glucose oxidase ($\beta$-D-glucose:oxygen oxidoreductase, of enzyme classification EC 1.1.3.4) is a well known type of enzyme. Bacterial glucose dehydrogenase is of more recent discovery, and is believed to be a quinoprotein with a polycyclicquinone prosthetic group (PQQ). Reference is made to Duine et al TIBS, (Oct. 1981) 278-280 and Arch. Microbiol (1982) 131.27-31.

Use of such a bacterial glucose dehydrogenase in the present invention has certain advantages over the use of a glucose oxidase. The major advantage is that it can give an oxygen-insensitive glucose sensor, since the enzyme does not use oxygen as an electron acceptor. A suitable enzyme can be purified (as described in more detail below) either by conventional chromatographic techniques or by two-phase aqueous partition from a range of micro-organisms. A preferred micro-organism is *Acinetobacter calcoaceticus* but various Gluconobacter species (e.g. *Gluconobacter oxidans*) or Pseudomonas species (e.g. *Pseudomonas fluorescens, Pseudomonas aeruginosa*) can also be used.

Mediator compounds which may be used in accordance with the invention are of different chemical types but all possess the electron-transfer property referred to above.

1. The mediator may for example be a polyviologen, for example, the type of material described in J. Polym. Sci. 13 pp 1–16 (1975), J. Appln. Polym. Sci. 24 pp 2075–85 (1979) or J. Polym. Sci. 17 pp 3149–57 (1979). A specific preferred polyviolgen is that compound made from o-dibromo xylene and 4.4'-bipyridyl, according to the following reaction:

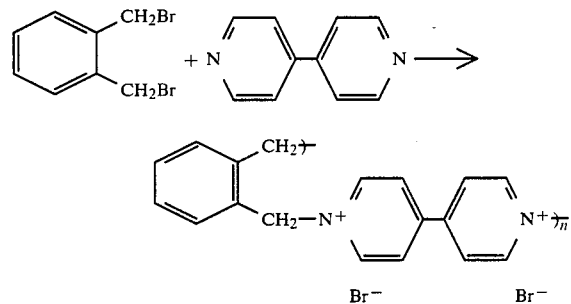

and described in Polymer Letters 9 pp 289–295 (1971).

Such polyviologen material, as described below, can be coated over or bonded to electrodes. It may include in its molecule longchain alkyl groups to increase its molecular weight and thus decreases its mobility.

2. The mediator may be a low-molecular weight compound of the group comprising chloranil, fluoranil or bromanil. The ortho-substituted isomers; and especially o-chloranil, are preferred within this class.

3. A particular preferred form of mediator compound is a ferrocene or ferrocene derivative.

A ferrocene has, as its fundamental structure, an iron atom held "sandwiched" by dative bonds between two pentadienyl rings. It is an electroactive organometallic compound, acting as a pH-independent reversible one-electron donor. As used, herein the term "a ferrocene" includes various derivatives (e.g. with various substituents on the ring structure, possibly in polymer form) differing in redox potential, aqueous solubility and bonding constant to glucose oxidase or bacterial glucose dehydrogenase enzyme.

For instance, the redox potential of the parent compound is +422 mV vs NHE. By introducing functional groups on to the ring system, E'o can be varied between +300 and +650 mV. Moreover, the water-solubility of the carboxyl-substituted ferrocenes is greater than that of the parent compound. Further description will be found in Kuwana T., 1977, ACS Symposium Series, 38, 154.

Among specific mediator compounds of this type are ferrocene itself, 1,1'-ferrocene dicarboxylic acid, dimethyl ferrocene, and polyvinyl ferrocene, e.g. of average molecular weight of about 16000.

4. Among further classes of mediator compounds for use in the present invention there figure
   (a) compounds of biological origin and hence general compatibility with any proposed in vivo use, e.g. Vitamin K
   (b) alkylsubstituted phenazine derivatives.

The electrically conductive material of the electrode itself can be a metal, particularly silver, or carbon either as a pre-formed rod or as an electrode shape made up from a paste of carbon particles. Surface condition of the electrode is usually important. If metal, the surface can be roughened where it contacts the active materials (enzyme and/or mediator). If solid carbon, the surface can be "oxidised" i.e. previously heat-treated in an oven with oxygen access.

Of the two types of enzyme listed, the dehydrogenase is preferred, and of the mediators the ferrocene-type compounds are preferred.

Certain combinations of the above materials, and certain configurations of electrode, are preferable in practice.

Polyviologens may be used with metallic electrodes. In one modification the invention envisages a metal electrode (preferably silver and with a roughened surface) coated with a mixture of glucose oxidase and a polyviologen described above, for example, in an agar layer and having a dialysis membrane located over this coating in order to prevent loss of active material while still allowing passage of the small glucose molecules.

Another modification of the invention provides a metal electrode coated with a stable film of glucose oxidase and a polyviologen co-immobilised on the metal surface e.g. by albumen and glutaraldehyde.

Yet another modification of the invention envisages a conductive electrode made of or including material to which a polyviologen is covalently bonded and further combined with glucose oxidase. The large polyviologen molecule projects from the electrode surface and this is believed to facilitate interaction with the enzyme.

In that form of the invention using polyviologens, as exemplified in the three modifications above, it is an objective to keep loss of active material (enzyme or mediator) to a very low level i.e. by the surrounding membrane, co-immobilisation or covalent bonding. In a different form of the invention, however, still using glucose oxidase, a rather higher level of loss of active material is tolerated, giving a sensor electrode of reduced but still useful life, coupled with improve sensitivity and selectivity.

In this form of the invention the electrode is composed of particulate carbon mixed with a low molecular weight mediator disseminated throughout the electrode and glucose oxidase. Chloranil and/or fluoranil are useful mediator substances. It is envisaged to construct from such an electrode a replaceable sensor tip to a needle-type probe for projecting only into the dermis so as to allow ready replacement.

Optionally, enzyme immobilisation materials, or polymeric electrode admixtures e.g. TEFLON, or long-chain alkyl derivatives of mediators of increased molecular weight and thus decreased mobility, can be incoporated.

In a particularly valuable form of the invention, however, the electrode comprises a carbon core, a layer of ferrocene or a ferrocene derivative at a surface thereof and a layer of glucose oxidase or glucose dehydrogenase at the surface of the ferrocene layer. The enzyme layer is preferably immobilised at the surface of the underlying mediator, retained in a self-sustaining gel layer thereupon and/or has a retention layer thereover permeable to the glucose moleculer.

The carbon core can itself be solid or a stiff paste of particles. Normally, it will present a smooth surface for the ferrocene or ferrocene derivative, which may be adhered thereto in a number of ways, for example,
   (a) For a monomeric ferrocene or ferrocene derivative, by deposition from a solution in a readily evaporatable liquid e.g. an organic solvent such as toluene.
   (b) For a ferrocene polymeric derivative, deposition from a readily evaporable organic solvent for the polymer such as chloroform. J. Polymer Sci. 1976, 14 2433 describes preparation of a polyvinyl ferrocene of average molecular weight about 16000 which can be deposited in this way.
   (c) For a polymerisable ferrocene-type monomer, by electrochemically induced polymerisation in situ, e.g. by dissolving vinyl ferrocene in an organic electrolyte containing tertiary butyl ammonium perchlorate in concentration about 1M and depositing at a potential of $-700$ mV vinyl ferrocene radicals as a polymer in situ.
   (d) By covalent modification of the carbon electrode e.g. by carbo-diimide cross-linking of the ferrocene or ferrocene derivative on to the carbon.

The enzyme to be coated on to the ferrocene or ferrocene derivative can be the glucose oxidase or the bacterial glucose dehydrogenase. The glucose oxidase can be immobilised to the underlying surface e.g. by the carbo-diimide material DDC (1-cyclohexyl-3-(2-morpholino ethyl)carbo-diimide metho-p-toluene sulphonate) which gives a thin strongly bound layer, a good linear response to low glucose concentrations, and oxygen insensitivity (because of the competition from the ferrocene with oxygen for electrons transferred to the enzyme redox centre from the substrate). Using DDC immobilisation of glucose oxidase on ferrocene also extends the top end of the linear range of the sensor from about 2 mM to 40 mM.

Other methods of immobilisation, or other forms of protection e.g. incorporated into a self-supporting gelatine layer, are also possible.

The bacterial glucose dehydrogenase can also be immobilised at the mediator surface, but may be merely deposited from an evaporatable solution, or held in a gelatin layer.

Optionally, but preferably when being used on live blood, a protective membrane surrounds both the enzyme and the mediator layers, permeable to water and glucose molecules. This can be a film of dialysis membrane, resiliently held e.g. by an elastic O-ring. It can however also with advantage be a layer of cellulose acetate, e.g. as formed by dipping the electrode into a cellulose acetate solution in acetone.

It will be apparent that while the invention has primary relevance to a sensor electrode, especially such an electrode specific for glucose, it also relates to the combination of such an electrode and temporary or permanent implantation means, e.g. a needle-like probe. Also, such an electrode, connected or connectable, with signal or control equipment, more especially with an insulin administration means, constitutes an aspect of the invention. Moreover, a method of monitoring a diabetic subject involving the use of a temporarily or permanently implanted electrode as described above is also within the scope of the invention.

The electrodes according to the invention permit the manufacture of an improved macro-sensor for use in hospital analytical glucose-sensing instruments of the existing type. The advantages compared to known instruments would be that the increased linear range together with very low oxygen sensitivity would allow omission of the dilution step involved in blood analysis in current instruments. Moreover, as described in more detail below, the response times of such electrodes are short (24-36 seconds for 95% of steady state depending on complexity of solution).

The electrodes of the invention, on the macro-scale could be incorporated into simple, cheap electronic digital read-out instruments for doctors surgeries or diabetic home-testing kits.

Use of a small version of the macro-sensor would be possible in a device which automatically takes a blood sample from the finger, brings it into contact with the sensor, amplifies the signal and gives a digital readout. Use of a micro-version of the sensor in a watch type device for monitoring glucose interstitial fluid in the skin could also be envisaged. It would be worn on the wrist and would have a disposable sensor cartridge in the back with one or more separate, fine, needle-type sensors. Each would feed into the electronics which if several sensors were used would cross-refer the current inputs to ensure reliability.

Connection of such devices to external insulin delivery systems could act as a feedback control loop for an insulin pump. Indeed, such a device could be housed in the canula used to feed insulin into the body from a pump and again serve as a sensor for the feedback loop. Other uses such as a hypoglycaemia alarm, or digital read-out monitor, are also possible.

BRIEF DESCRIPTION OF THE DRAWING

The invention will be further described with reference to the following Examples 1 to 3 and to the accompanying drawings, in which.

DESCRIPTION OF THE PREFERRED EMBODIMENTS

EXAMPLE 1

Figure 1:
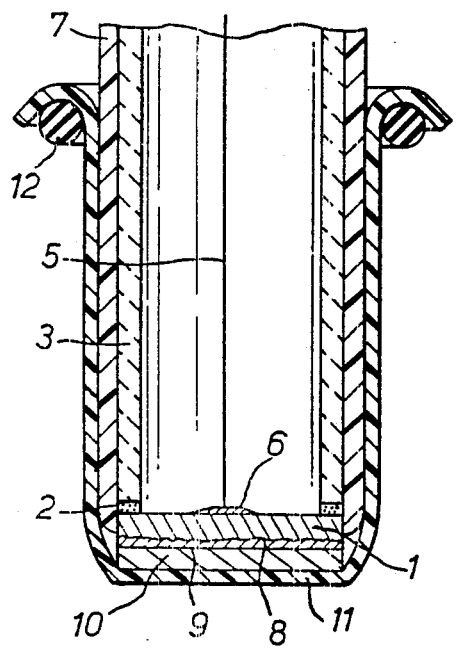
FIG. 1 is a diagrammatic longitudinal cross-section through a glucose sensor electrode.

Purification of Quinoprotein Glucose Dehydrogenase (GDH) from *Acinetobacter calcoaceticus*

(a) Growth of Organisms

Strain NCTC 7844 was grown on sodium succinate (20 gl$^{-1}$) in batch culture at pH 8.5 and 20° C. Cells were harvested after 20 hours $A_{600}=6.0$) using a Sharples centrifuge, and stored frozen.

(b) Purification of Glucose Dehydrogenase

The method is based on the method of J A Duine et al (Arch Microbiol, 1982 vide supra) but with modifications as follows.

1. 100 g. of cells were thawed, resuspended in 3 300 ml. of 56 mM Tris/39 mM glycine and treated for 20 minutes at room temperature with 60 mg. lyxozyme.

2. Triton X-100 extracts were combined and treated with 0.01 mgml$^{-1}$ of deoxyribonuclease I for 15 minutes at room temperature. The resulting suspension was then centrifuged at 48,000 xg for 25 minutes at 4° C. The supernatant from this centrifugation was then treated with ammonium sulphate. The yellow protein precipitating between 55 and 70% ammonium sulphate was resuspended in 36 mM Tris/39 mM glycine containing 1% Triton X-100 and dialysed against that buffer at 4° C. for 5 hours.

3. Active fractions from the CM sepharose C1-6B column were combined and concentrated using Millipore CX-30 immersible ultrafilters.

EXAMPLE 2

Purification of Quinoprotein Glucose Dehydrogenase from *Acinetobacter calcoaceticus* (alternative method)

(a) Growth of Organisms

The method of Example 1 was repeated.

(b) Purification of GDH

The method is based on the partitioning of proteins between two liquid phases. The steps were:

1. Cells were thawed and resuspended at 3 ml/g wet weight in 50 mM sodium phosphate, pH 7.0. They were then pre-cooled on ice and passed once through a Stansted pressure cell (made by Stansted Fluid Power Ltd., Stansted, Essex, UK) at 25,000 psi. This provided the cell-free extract.

2. The cell-free extract was then mixed for 15 minutes at room temperature with 50% (w/v) polyethyleneglycol 1000, 50% (w/v) sodium phosphate, pH 7.0 and distilled water in the proportions of 2:4:3:1 respectively. This mixture was centrifuged at 5000 rpm for 5 minutes to break the emulsion.

3. The lower layer was aspirated off and desalted immediately, by either diafiltration using an Amicon hollow-fibre ultrafiltration cartridge of 10000 mwt cut off, or by passage through a Sephadex G50 (medium grade) gel filtration column.

4. The resulting solution was concentrated using an Amicon PM10 membrane in a nitrogen pressure cell.

EXAMPLE 3

Interaction between ferrocene and glucose oxidase

DC cyclic voltammetry was used to investigate the homogeneous kinetics of the reaction between ferrocene and the glucose oxidase enzyme under substrate excess conditions. A two compartment electromechemical cell of 1.0 ml volume fitted with a Luggin capillary was used. The cell obtained at 4.0 mm gold disc working electrode, a platinum gauze counter-electrode and a saturated calomel electrode as a reference. A series of voltamograms for ferrocene was recorded at scan rates of 1–1000 mVs$^{-1}$ in 50 mM potassium phosphate buffer, pH 7.0. The data showed that the mediator acted as a reversible, one-electron acceptor $E_o{}^1 = +165$ MV SCE.

Addition of 50 mM glucose has no discernable effect on the electrochemistry of the mediator (500 μm). Upon addition of glucose oxidase (10 μm), however, an enhanced anodic current was observed in the voltamogran at oxidising potentials with respect to the mediator. This indicated catalytic regeneration of the reduced form of the mediator by glucose oxidase. Quantitative kinetic data was obtained for this reaction using an established procedure (Nicholson, R. S. and Shain, J., 1964, *Anal. Chem.*, 36, 707). The mediator gave a second order rate constant for the reaction between ferricinium ion and reduced glucose oxidase of $K = 10^4$ m$^{-1}$s$^{-1}$. This ability of the ferricinium ion to act as a rapid oxidant for glucose oxidase facilitates the efficient coupling of the enzymic oxidation of glucose.

EXAMPLE 4

The procedure of Example 3 was repeated using 1,1'-ferrocene dicarboxylic acid instead of ferrocene. The value of Eo' was determined to be +420 mV, and the second order rate constant of the ferricinium ion and reduced glucose oxidase was again $10^4$ m$^{-1}$S$^{-1}$, thus confirming the conclusions drawn from Example 3.

EXAMPLE 5

Glucose oxidase/polyviologen

For experimental purposes an in vitro sensor was made up as shown in FIG. 1.

A silver disc 1 was glued at 2 over the lower end of a length of 12 mm glass tubing 3. A wire 5 was soldered to the back of the silver disc at 6. The tubing was placed inside a "Teflon" sleeve 7, and the outside of the disc 1 roughened at 8. A solution containing glucose oxidase and the o-dibromo xylene/4,4'bipyridyl polyviologen was applied over the roughened surface 8 and dried to layer 9. A subsequent layer 10 of molten agar also containing the glucose oxidase and polyviologen, of approximately 1 mm in thickness was placed over the layer 9, and solidified. Finally, dialysis membrane 11 was placed over the assembly and held by O-ring 12.

To demonstrate the principle of using the polyviologen mediator to couple electrically the glucose oxidase to an electrode, the sensor was placed in a buffered electromechanical cell, which was stirred and agitated with a current of nitrogen. The electrode was held at −90 vM vs SCE, and current flow measured on a chart recorder. Aliquots of glucose were added. As the glucose concentration in the solution increased, over the range of 1 to 8 mM, the current also increased, indicating that the electrode was acting as a glucose sensor.

EXAMPLE 6

Glucose oxidase/Chloranil

Chloranil (10 mg) was mixed with carbon powder (1.5 g) and NUJOL (1 ml) to form a paste and used as an electrode in a similar liquid system to the above. The electrical coupling between the enzyme and electrode was so effective that the enzyme preferentially reduced the electrode rather than the oxygen, so that the system was oxygen-insensitive. The current response was linear over the 1–10 mM glucose concentration range.

EXAMPLE 7

Glucose/Oxidase Dimethyl Ferrocene

Mini electrode for in vivo glucose sensing in skin

Figure 2:
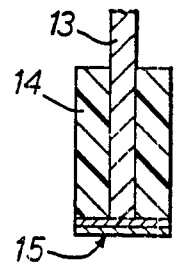
FIG. 2 is a diagrammatic longitudinal cross-section through a different form of glucose sensor electrode.

A graphite rod 13 (FIG. 2) with an oxidised surface, 30 mm long × 0.9 mm diameter is glued with epoxy resin into a nylon tube 14 25 mm long, 0.9 mm inside diameter, 1,3 mm outside diameter. The end 15 of the electrode is dipped into a solution of dimethyl ferrocene, (10 mg/ml) in toluene, and the solvent is then allowed to evaporate.

The end 15 of the electrode is placed into a solution of water soluble DCC (25 mg/ml) in acetate buffer, pH 4.5 for 1 hour. It is then rinsed, in buffer only, for 5 minutes and thereafter placed in a solution of glucose oxidase (10 mg/ml) in acetate buffer, ph 5.5, for 1½ hours before again rinsing in buffer. The tip of the electrode 15, with the layers of dimethyl ferrocene and immobilised enzyme is then dipped into a solution of cellulose acetate dissolved in acetone and formamide and put into ice water for several minutes, to give a protected and stable electrode.

Figure 3:
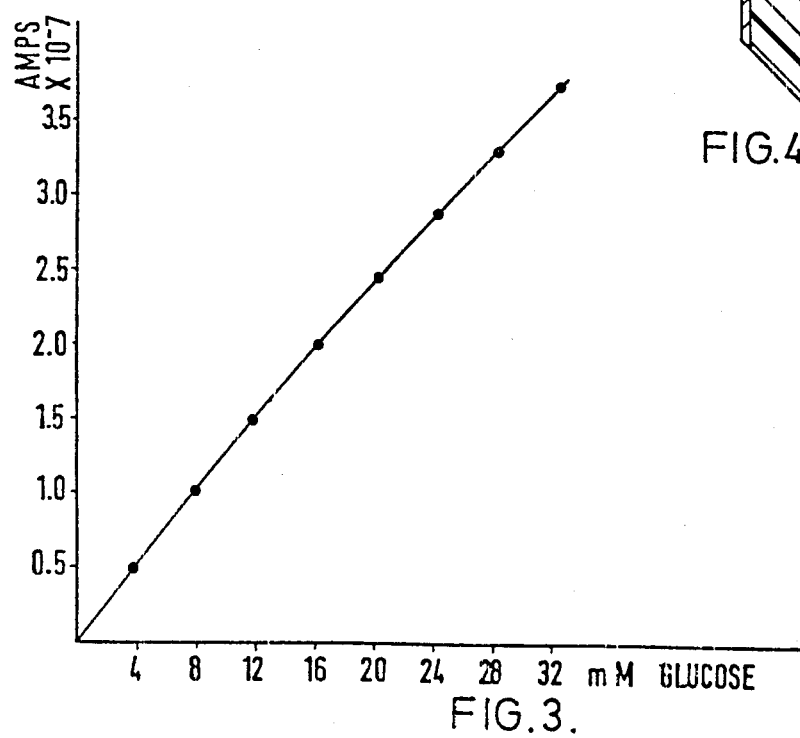
FIG. 3 is a graph of the current sensed by the electrode of FIG. 2, against glucose concentration.

This electrode was connected to a potentiostat, together with a suitable counter electrode and calomel reference electrode and placed in a solution containing glucose. The potential of the working electrode is kept at +100 mV to 300 mV relative to the calomel electrode, i.e. as low as possible to avoid oxidation of potentially interfering substances. A current is produced which is proportional to the glucose concentration. The time for 95% of response is less than 1 minute and the electrode gives a near linear response over the range 0–32 mM glucose, as shown in FIG. 3. Slow loss of activity ferrocene (due to slow loss of ferrocinium ion) can be minimised by keeping the electrode at a potential between 0 and −100 mV vs. a standard calomel electrode when not in use.

Figure 4:
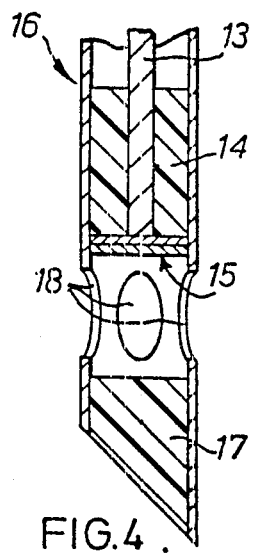
FIG. 4 is a diagrammatic longitudinal cross-section of the electrode of FIG. 2 located within a hypodermic needle.

FIG. 4 shows in section an electrode structure in which an electrode (references as in FIG. 2) of much smaller size is held within a hypodermic needle 16 plugged at its point 17 but with side windows 18 for passage of blood or other body fluid. The small size of such an electrode and its linear response over a large range of glucose concentrations makes it possible to use the electrode for in vivo glucose determination on both severely diabetic and normal individuals.

EXAMPLE 8

Glucose Oxidase/Ferrocene

In vitro sensor

A carbon rod 19 (FIG. 5) Ultra carbon, grade U5, 6 mm × 15 mm) with a metal connector 20 secured in one end was sealed in glass tubing 21 (borosilicate, 6 mm i.d. × mm) with an epoxy resin (araldite). (not shown). The exposed surface at 22 was polished with emery paper and washed with distilled water. The entire rod was heated in an oven for 40 h at 200° C. to given as oxidised surface at 22.

15 μl of ferrocene (20 mg/ml in toluene) was pipetted onto the oxidised surface and allowed to dry completely. The rod was then placed in 1 ml of water-soluble DCC (25 mg/ml in 0.1M acetate buffer, ph 4.5) for 80 min at room temperature. The rod was then washed in 0.2M carbonate buffer, pH 9.5 and placed in a glucose oxidase solution (Sigma type X, 12.5 mg/ml) for 1½ hours at room temperature. It was finally washed with water with a pH 7 buffer containing 0.2 g/l glucose) and stored at 4° C.

Figure 6:
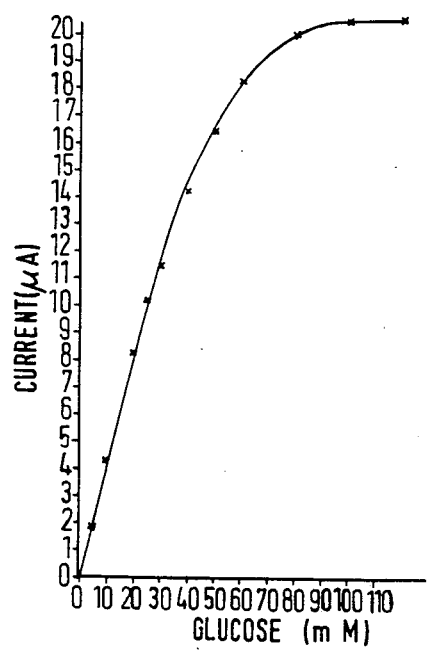
FIG. 6 is a graph analogous to FIG. 3 for the electrode of FIG. 5.

The characteristics of the above electrode were determined in a nitrogen-saturated buffer solution (0.2M $NaPO_4$, pH 7.3) and are shown in FIG. 6. The curve is linear from 2 to 25 mM glucose and reaches saturation current at 100 mM in glucose.

In separate tests with an air-saturated buffer at 8 mM glucose the current was measured as being at least 95% of that produced in the nitrogen-saturated buffer.

Response time was also measured, being the time taken to achieve 95% of maximum current for the given glucose concentration. With the nitrogen-saturated buffer an electrode as described above had a response time of 24 seconds at 2 mM glucose and 60 seconds at 6 mM glucose. With the same buffer, such an electrode modified by a cellulose acetate membrane coating (produced as in Example 7) gave response times of 36 seconds (2 mM) and 72 seconds (6 mM). With blood, this modified electrode gave response times of 36 seconds (blood with a known 2 mM glucose content) and 72 seconds (blood at a known 6 mM glucose content).

Electrodes as above were stored in 20 mM $NaPO_4$, pH 7 for 4 weeks at 4° C. as a stability test and thereafter re-examined as above. The results were within 10% and usually within 5% of results with a freshly made electrode.

EXAMPLE 9

Glucose Dehydrogenase/Ferrocene

A stiff carbon paste was made up from 1.6 g of Durco activated charcoal and 2.5 ml of liquid paraffin. A Pasteur pipette of 6 mm internal diameter was blocked 2 mm from its wide end by a silver disc to which a connecting wire was soldered. The space between the disc and the end of the pipette was filled with the carbon paste, and the surface of the paste was polished with paper until smooth and even.

A single 20 microliter drop of a toluene solution of ferrocene (20 mg/l) was placed on the smooth surface and allow to spread and evaporate to leave a film of the ferrocene.

A further drop of 25 microliters of bacterial glucose dehydrogenase solution as obtained in Example 1, containing between 1 and 10 mg. of protein per ml, was placed on this ferrocene surface and allowed to spread.

A cover of dialysis membrane was secured over the so-coated end of the electrode by a tight-fitting O-ring.

EXAMPLE 10

Glucose Dehydrogenanse/Ferrocene

The procedure of Example 9 was repeated but using as electrode the same carbon paste packed into the space defined between the end of a length of nylon tubing and a stainless steel hypodermic needle shaft inserted therein terminating 2 mm. short of the tubing end, so as to define a small electrode body. The electrode was further fabricated using only 5 microliters of the ferrocene solution and 1 microliter of the enzyme solution.

EXAMPLE 11

Glucose Dehydrogenase/Ferrocene

Figure 5:
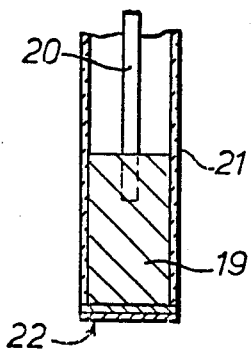
FIG. 5 is a diagrammatic longitudinal cross-section through a yet further glucose sensor electrode.

The procedure of Example 9 was repeated using as electrode a solid carbon rod (Ultracarbon grade U5 6 mm diameter) within a Pyrex glass tube 3 cm long and 6 mm internal diameter and connected to a stainless steel hypodermic shaft, giving a construction similar to that shown in FIG. 5. The end of the carbon rod was polished smooth with emery cloth and aluminium oxide powder prior to the application of the ferrocene solution.

EXAMPLE 12

Glucose Dehydrogenase/Ferrocene

A gelation-entrapped glucose dehydrogenase was prepared by mixing at 37° C., 25 mg gelatin, 0.5 ml of the glucose dehydrogenase solution as described in Example 9 and 2.5 microliters of TEMED. After complete dissolving of the gelatin 200 microliters of the solution was spread over an area of 2 $cm^2$ and allowed to dry under a stream of cold air.

A disc of 0.25 $cm^2$ area was then used instead of the drop of enzyme solution in Example 9.

EXAMPLE 13

Glucose Dehydrogenase/Ferrocene

Example 12 was repeated using a disc of the gel of 1 $mm^2$ area and applying it instead of the drops of enzyme solution in the construction of example 10.

Figure 7:
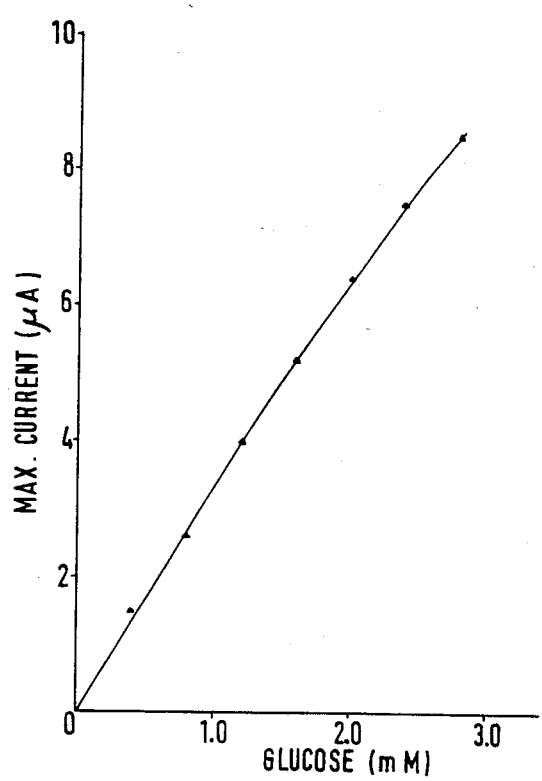
FIG. 7 is a graph analogous to FIG. 3 for an electrode incorporating a glucose dehydrogenase.

The results obtained from the electrodes described in Examples 9 to 13 are all similar, and show a very specific electrode of low oxygen sensitivity. By way of example, the electrode of Example 12 was calibrated and gave the results shown in FIG. 7.

Devices such as shown in the Examples offer advantages over most of the enzyme-based sensors current available. When compared to such sensors prior to dilution steps, the present electrode has an equal or faster response time, the ability to operate under anaerobic conditions, greater oxygen insensitivity (important in blood samples, where oxygen concentration is variable), extended linear range covering the complete physiological range and comparable specificity, stability and ease of manufacture.

We claim:

1. A sensor electrode for use in a liquid mixture of components, said electrode being responsive to the presence of at least one selected component of said mixture capable of undergoing an enzyme-catalysed reaction, the electrode being composed of electrically conductive material and comprising, at least at an external surface thereof, the combination of an enzyme and a mediator comprising a ferrocene which transfer electrons between the enzyme and the conductive material of the electrode when the enzyme is catalytically active to provide a current representative of said activity.

2. A sensor electrode as claimed in claim 1 in which the enzyme catalyses a reaction of glucose whereby there is provided a glucose sensor.

3. A sensor electrode as claimed in claim 2 in which the enzyme is a glucose oxidase.

4. A sensor electrode as claimed in claim 2 in which the enzyme is a bacterial glucose dehydrogenase.

5. A sensor electrode as claimed in claim 4 in which the glucose dehydrogenase is that separated from *Acinetobacter calcoaceticus*.

6. A sensor electrode as claimed in any of claims 1 to 5 in which the mediator is chosen from ferrocene, 1,1'-ferrocenedicarboxylic acid, dimethyl ferrocene, and polyvinyl ferrocene.

7. A sensor electrode as claimed in any of claims 1 to 5 in which the electrode is made of a material chosen from silver, carbon particle paste and solid carbon.

8. A sensor electrode as claimed in claim 7 wherein said electrode comprises solid carbon, a layer of ferrocene at an external surface thereof, and an enzyme located upon said ferrocene layer.

9. A sensor electrode as claimed in claim 8 in which the ferrocene is deposited on the surface from a readily evaporatable organic solvent therefor.

10. A sensor electrode as claimed in claim 9 in which the ferrocene is bonded to the solid carbon by carbo-diimide cross-linking.

11. A sensor electrode as claimed in claim 8 in which the ferrocene is in polymeric form and produced at the surface by polymerisation of the corresponding monomer.

12. A sensor electrode as claimed in claim 8 having an outermost protective membrane permeable to water and glucose molecules, said membrane covering said enzyme located upon said ferrocene layer.

13. A sensor electrode as claimed in claim 12 in which the protective membrane is a layer of cellulose acetate deposited from a solution thereof.

14. A sensor electrode for use in a liquid mixture including glucose, to provide a current representative of the presence of glucose therein, the electrode consisting essentially of solid carbon, a layer of ferrocene-type compound at an external surface thereof as an electron-transferring mediator, and an enzyme which is glucose oxidase or bacterial glucose dehydrogenase located upon said mediator layer.

15. A sensor electrode as claimed in claim 14 in which the enzyme is a glucose oxidase immobilised on the mediator by DCC.

16. A sensor electrode as claimed in claim 14 in which the enzyme is a bacterial glucose dehydrogenase deposited on the mediator layer from an evaporatable solution.

17. A sensor electrode as claimed in claim 14 in which the enzyme is a bacterial glucose dehydrogenase held in a gelatine layer at the surface of the mediator layer.

18. A sensor suitable for implantation comprising a sensor electrode and means for implantation of said sensor electrode in a human subject, said sensor electrode being responsive to the presence in said subject of at least one selected component capable of undergoing an enzyme-catalyzed reaction, said electrode being composed of electrically conductive material and comprising, at least at an external surface thereof, the combination of an enzyme, and a mediator comprising a ferrocene which transfers electrons between the enzyme and the conductive material of the electrode when the enzyme is catalytically active to provide a current representative of said activity.

19. The sensor of claim 18 in which the implantation means is a needle-like probe carrying said sensor electrode thereon.

* * * * *

UNITED STATES PATENT AND TRADEMARK OFFICE
CERTIFICATE OF CORRECTION

PATENT NO. : 4,545,382

DATED : October 8, 1985

INVENTOR(S) : Irving J. Higgins et al

It is certified that error appears in the above-identified patent and that said Letters Patent is hereby corrected as shown below:

```
Column 6, line 56, "polyethyleneg-lycol" should
    be --polyethylene-glycol--;

Column 10, line 42, "current" should be --currently--;

Column 10, line 60, "transfer" should be --transfers--.
```

Signed and Sealed this

Fourteenth Day of January 1986

[SEAL]

Attest:

Attesting Officer

DONALD J. QUIGG

Commissioner of Patents and Trademarks